(12) United States Patent
Ruddell et al.

(10) Patent No.: US 9,201,065 B2
(45) Date of Patent: Dec. 1, 2015

(54) AGGLUTINATION ASSAY

(75) Inventors: Carolyn Jennifer Ruddell, Wirral (GB);
Gerald John Allen, Caythorpe (GB);
Douglas Robert Evans, Chester (GB);
Elizabeth Burke, Wigan (GB)

(73) Assignee: Platform Diagnostics Limited, Liverpool (GB)

( * ) Notice: Subject to any disclaimer, the term of this patent is extended or adjusted under 35 U.S.C. 154(b) by 655 days.

(21) Appl. No.: 12/093,440

(22) PCT Filed: Nov. 13, 2006

(86) PCT No.: PCT/GB2006/004204
§ 371 (c)(1),
(2), (4) Date: May 12, 2008

(87) PCT Pub. No.: WO2007/054714
PCT Pub. Date: May 18, 2007

(65) Prior Publication Data
US 2008/0248504 A1     Oct. 9, 2008

(30) Foreign Application Priority Data

Nov. 12, 2005 (GB) .................. 0523124.6
Jun. 3, 2006 (GB) .................. 0610973.0

(51) Int. Cl.
*G01N 33/558*   (2006.01)
*G01N 33/563*   (2006.01)
*G01N 33/543*   (2006.01)

(52) U.S. Cl.
CPC ........ *G01N 33/54313* (2013.01); *G01N 33/558* (2013.01)

(58) Field of Classification Search
CPC .......... G01N 33/54313; G01N 33/555; G01N 33/80; G01N 33/531; G01N 33/541; A61K 2039/505; Y10S 436/808; Y10S 436/81; Y10S 530/806
USPC ......... 436/514, 518, 519, 520, 524, 529, 808, 436/810; 435/287.1, 287.7; 422/56, 57, 61
See application file for complete search history.

(56) References Cited

U.S. PATENT DOCUMENTS

| | | | |
|---|---|---|---|
| 3,951,606 A | | 4/1976 | Moyer et al. |
| 4,233,402 A | * | 11/1980 | Maggio et al. .................. 435/5 |
| 4,308,026 A | | 12/1981 | Mochida et al. |
| 4,391,904 A | * | 7/1983 | Litman et al. ................. 435/7.91 |
| 4,433,059 A | * | 2/1984 | Chang et al. ................... 436/512 |
| 4,459,361 A | | 7/1984 | Gefter |
| 4,552,839 A | | 11/1985 | Gould et al. |
| 4,663,278 A | | 5/1987 | DiNello |
| 4,666,863 A | | 5/1987 | Edwards et al. |
| 4,894,347 A | | 1/1990 | Hillyard et al. |
| 5,202,267 A | | 4/1993 | Ditlow et al. |
| 5,231,035 A | | 7/1993 | Akers, Jr. |
| 5,413,913 A | | 5/1995 | Hillyard et al. |
| 5,451,507 A | | 9/1995 | Skold et al. |
| 5,543,332 A | * | 8/1996 | Lihme et al. .................. 436/528 |
| 5,565,366 A | | 10/1996 | Akers, Jr. |
| 5,573,919 A | * | 11/1996 | Kearns et al. .................. 435/7.9 |
| 5,627,078 A | | 5/1997 | Karl et al. |
| 5,656,503 A | | 8/1997 | May et al. |
| 5,827,749 A | | 10/1998 | Akers, Jr. |
| 5,877,028 A | * | 3/1999 | Chandler et al. .............. 436/514 |
| 5,972,625 A | * | 10/1999 | Rosen et al. ................... 435/7.2 |
| 6,136,545 A | * | 10/2000 | Hosel et al. .................... 435/7.1 |
| 6,235,241 B1 | | 5/2001 | Catt et al. |
| 6,274,325 B1 | | 8/2001 | Deger et al. |
| 6,472,226 B1 | | 10/2002 | Barradine et al. |
| 2002/0187071 A1 | | 12/2002 | Law |
| 2003/0003602 A1 | | 1/2003 | Vogt et al. |
| 2004/0248222 A1 | | 12/2004 | Root et al. |
| 2005/0069967 A1 | | 3/2005 | Sumida et al. |
| 2005/0079040 A1 | | 4/2005 | Perlstein |

FOREIGN PATENT DOCUMENTS

| | | |
|---|---|---|
| EP | 0174195 A1 | 3/1986 |
| EP | 0293779 A1 | 12/1988 |
| EP | 0297292 A2 | 1/1989 |
| EP | 0310872 A1 | 4/1989 |
| EP | 0323909 A1 | 7/1989 |
| EP | 0556202 A1 | 4/1992 |
| EP | 0516529 A2 | 12/1992 |
| EP | 0280559 B1 | 10/1993 |
| EP | 0596104 A1 | 12/1993 |
| EP | 0308242 B1 | 1/1995 |
| EP | 0556202 B1 | 5/1997 |
| EP | 0818680 A1 | 1/1998 |
| EP | 0962771 B1 | 4/2003 |
| GB | 2045431 A | 10/1980 |
| JP | 05-249117 | 9/1993 |
| JP | H10 19893 A | 1/1998 |
| JP | 2001-159632 | 6/2001 |
| WO | 90/09596 A1 | 8/1990 |
| WO | 9104492 A1 | 4/1991 |
| WO | 93/24630 A1 | 12/1993 |
| WO | 9415193 A1 | 7/1994 |
| WO | 99/35497 A2 | 7/1999 |
| WO | 01/31337 A2 | 5/2001 |
| WO | 0204484 A2 | 1/2002 |
| WO | 02/40698 A2 | 5/2002 |
| WO | WO2004/083859 | * | 9/2004 | ............ G01N 33/53 |
| WO | 2005/012870 A2 | 2/2005 |
| WO | WO 2005/079420 A2 | 9/2005 |

* cited by examiner

OTHER PUBLICATIONS

Gribnau et al. "Particle-Labelled Immunoassays: A Review." Journal of Chromatography, Elsevier Publishing Company, Amsterdam, NL, vol. 376, pp. 175-189 (1986).

*Primary Examiner* — Shafiqul Haq
*Assistant Examiner* — Carmencita M Belei
(74) *Attorney, Agent, or Firm* — Speckman Law Group PLLC; Janet Sleath

(57) ABSTRACT

The invention relates to agglutination assays and related kits, reagents and devices. In particular methods of assaying small analytes having few epitopes are disclosed, by means of using hub moieties to which multiple analytes may be bound by a first epitope, together with a further moiety capable of binding a second analyte epitope and which is also capable of binding to a detectable particle. Stable agglutinated complexes may be so formed, which may used as the basis for various assay formats.

17 Claims, 4 Drawing Sheets

AGGLUTINATION ASSAY

REFERENCE TO RELATED APPLICATIONS

This application is the US national phase entry of International Patent Application No. PCT/GB2006/004204, filed Nov. 13, 2006, which claims priority to UK Patent Applications No. 0523124.6, filed Nov. 12, 2005 and 0610973.0 filed Jun. 3, 2006.

FIELD OF THE INVENTION

The present invention relates to an agglutination assay for detection of analytes in a sample. In particular, the invention relates to porous carrier-based assays and assay devices, kits comprising means for conducting such assays, and assay methods for the detection of analyte in a sample.

BACKGROUND TO THE INVENTION

Immunoassays are a well established technique for detecting and quantifying analytes in samples. They are particularly useful for detecting and/or measuring substances in biological samples as an aid to disease diagnosis and prognosis, and for predicting a patient's response to therapy. Techniques such as the radioimmunoassay and enzyme immunoassay, which revolutionised diagnostic medicine, are based upon the detection of antibody-antigen interactions. Numerous detection systems are available, including the use of radio or enzyme labelled antigens, antibodies or complexes thereof. Many require incubation with specific substrates in order to measure the end-point calorimetrically, or by fluorescence.

Whilst these assays are sensitive, the detection systems are often complex, and therefore expensive. Typically, the assay systems require several washing steps, meaning that conventional assays are often unsuitable for point-of-care type assessment.

Agglutination immunoassays are well-known in the art, and rely upon agglutination of particles to which an antigen or antibody is bound to indicate the presence of the corresponding antibody or antigen in a sample. In one of the simpler forms of an agglutination assay, antibodies to a particular analyte are bound to a bead or other visible material (for example, polystyrene microparticles in the latex agglutination reaction). Typically, the antibody will be divalent, thus causing the latex beads to form clumps in the presence of an analyte. Such clumps indicate a positive result, and can be seen with the naked eye.

WO04/83859 describes a capillary based agglutination assay, comprising a capillary pathway which contains a reagent system capable of causing agglutination with the analyte. The reagent system comprises an antibody bound to either the capillary walls at a predetermined location, or antibody bound to beads which are placed in the capillary system at a predetermined location. Upon application to the capillary pathway, a sample flows along the pathway until it reaches the agglutination reagent system. If analyte is present, agglutination will occur, retarding further flow of the sample along the tube. Detection means for the presence of the sample at the downstream end of the pathway are effected after a predetermined time from application of the sample—if no sample can be detected, then analyte is present, indicating a positive result. This device uses latex beads as the agglutination means.

There is a growing need for assays to be performed closer to the patient, primarily to shorten the time taken to provide results. Such assays are known as Point-of-Care assays, and typically need to be robust and simple to perform since they are carried out in a non-laboratory setting, frequently by non-skilled staff. Ideally, they should be fully self-contained and require no ancillary equipment (with the possible exception of a reader). Point-of-Care assays need similar sensitivity to laboratory-based assays if they are to have any clinical use. However, conventional immunoassays often comprise complex protocols and detection systems, meaning that they are often unsuitable for point-of-care type use.

Specific Point-of-Care assays have been developed. The most common are lateral flow assays. Often, these are based on a labeled mobile component (e.g. coloured particle-labeled antibody), an immobilised component (e.g. antibody stripe or dot) and a membrane through which sample is caused to move by capillary action. In the presence of analyte, a "sandwich" is formed at the immobilised antibody capture zone, leading to development of a coloured line or dot. Conventional Lateral Flow Assays are exemplified by, for example, Unilever Patent Holdings B.V (U.S. Pat. No. 5,656, 503). These assays specify an immobilised antibody capture zone, albeit in a lateral flow format as opposed to the radial format taught by Geigel et al (Clin Chem 28(9) pp 1894-8, 1982).

Lateral flow assays offer many advantages, including speed, convenience, and relatively low-cost. However, they have several drawbacks. The antibody is generally immobilised by adsorption onto the membrane, so variations in membrane and/or antibody batch can lead to variations in the amount of antibody immobilised. Further, some of the antibodies may be only loosely bound and can become mobile when the fluid front passes, leading to loss of signal. Also, since one antibody is immobilised, the only time for it to react with the analyte is as the sample flows past, so sensitivity can be reduced due to the short incubation time. It is also necessary to produce specific coated membranes for each analyte, thus increasing manufacturing costs.

Attempts have been made to address these disadvantages by avoiding the use of an immobilised capture antibody. For example, Miles (EP 297292), Hygeia Sciences (EP 310872), and Mizuho (EP 0962771) describe systems involving a membrane with a trapping zone in conjunction with 2 antibody-coated particles, one unlabeled but large such that it is trapped by the zone, the other small and labeled which can pass through the zone. In the presence of analyte, the small beads become bound to the trapped large beads leading to formation of a coloured line. Although these methods avoid the use of an immobilised capture antibody, they require two populations of antibody-coated particles in addition to a trapping zone. Frequently such particles are hydrophobic in nature, and thus can be caused to aggregate in a non-specific manner in the presence of biological fluids.

Others have attempted a simpler format, whereby antibody-coated particles capable of free movement through a membrane are caused to agglutinate in the presence of analyte such that their movement is halted. Such agglutination-based immunoassays are known in the art, and rely upon agglutination of particles to which an antigen or antibody is bound to indicate the presence of the corresponding antigen or antibody in a sample. In one of the simpler forms of an agglutination assay, antibodies to a particular analyte are bound to a bead or other visible material.

In particular, Amersham (U.S. Pat. No. 4,666,863) discloses a method for separating free and bound label by chromatographic means. In one variant, they teach separation of agglutinated and non-agglutinated antibody-coated coloured particles using flow along a membrane. Prior to separation, the reaction mixture is reacted with a cross-linking agent to stabilise the agglutinate. Daiichi (EP 293779) also discloses a coloured latex agglutination reaction, where agglutinated and non-agglutinated particles are separated by a capillary which allows non-agglutinated latex through but traps the aggregates. Kodak (EP 280559) describes an assay for multivalent analytes whereby in the absence of analyte label can pass through a filter, but in the presence of analyte an agglutinate is formed which is trapped. Akers (EP 556202) describes a system in which a test mixture is formed by contacting the sample with coloured particles having analyte-specific receptors on their surface. The test mixture is passed through a filter having pores which are larger than the coloured particles but smaller than the particle-analyte aggregates, thus causing trapping of the aggregates. Presence of aggregates from the mixture is determined by checking the colour of the filtrate. Genosis (U.S. Pat. No. 6,472,226) describes a lateral flow assay without immobilised antibody for very large analytes. They describe a 2-zone system, one having large pores and one having small pores, such that analyte can pass through the large pores but becomes trapped on reaching the zone of small pores. This is used in conjunction with a small label (e.g. gold sol) which can pass through both zones. In the presence of analyte, a fraction of the gold sol becomes bound to the analyte and becomes trapped at the small pore zone.

Common point of care assays are membrane lateral flow assays, generally used on urine samples. Urine contains a limited number of analytes, and so the application of these assays is restricted. To be used on whole blood, which contains a far greater range of analytes, filtration is usually necessary to remove the blood cells, as otherwise blockage and discolouration of the membrane would occur.

As a result, assay systems have been developed for use with whole blood, which do not require filtration of the blood. In U.S. Pat. No. 4,433,059, Chang discloses a non-capillary agglutination immunoassay in which two antibodies are covalently linked "tail to tail" to facilitate an autologous agglutination reaction utilizing particles endogenous to the sample. One antibody is specific for an antigen borne by an indicator substance, such as an erythrocyte. This antibody is univalent, and thus non-specific agglutination is avoided. The other antibody is divalent and specific for the analyte. In the presence of analyte, the conjugate antibody will cross-link the analyte and erythrocytes producing an agglutination of the erythrocytes.

Agen in various patent application (U.S. Pat. No. 5,413,913, U.S. Pat. No. 4,894,347, WO93/24630 and EP308242) describe a non-capillary agglutination system for use with whole blood, where the erythrocytes of the blood sample are used as the agglutination particles. The system requires the use of a conjugate comprising two antibodies or antibody fragments, one of which is directed against an erythrocyte antigen and the other of which is directed against a multi-epitopic analyte. In the presence of analyte, the antibody will agglutinate the erythrocytes.

Capillary based agglutination systems using whole blood as the sample have been previously disclosed, for example by U.S. Pat. No. 3,951,606 and WO 99/35497. These both give an indication of the presence/amount of analyte by determining either the location of the agglutinate or which capillary is blocked. Both of these assays are reliant upon the agglutination causing a total blocking of the capillary.

In the majority of current agglutination assays, the aggregation of particles is detected visually. However, a visual end-point is subjective and it is difficult to record the data electronically.

An important consideration is that, in the main, these agglutination-based assays are restricted to the detection of large analytes with multiple epitopes which enable the formation of large, stable agglutinates. Their effectiveness with smaller analytes having fewer epitopes, or where only a limited number of available epitopes are being used, can be compromised as the reduced number of binding events may result in a weakened aggregate and loss of sensitivity.

The present invention aims to address or ameliorate some or all of the above-mentioned problems associated with the assay systems of the prior art.

SUMMARY OF THE INVENTION

The basis of the invention is to cause a stable, detectable agglutination reaction in the presence of analyte. For point-of-care assays, this is conveniently performed within a porous carrier or a device containing capillary tracks, although alternative methods are possible, particularly for laboratory-based assays Indeed, for such applications, wholly fluid phase formats based on, for instance, nephelometry, may be used. Although reasonable agglutination can be achieved using large, multi-epitopic analytes where multiple binding events are possible, it can be difficult to achieve stable agglutination with smaller analytes which may contain only a few epitopes. Indeed, for reasons of specificity, it is often desirable to only utilise two epitopes on an analyte.

To overcome this, the present invention provides a hub, which comprises multiple binding partners bound to a carrier. The resulting hub can bind several analyte molecules, in effect making the analyte appear multi-epitopic and amplifying its effective binding capacity. In this way it is possible to obtain strong, stable agglutination for small analytes and/or in those situations where only a restricted number of epitopes on the analyte are employed, reducing the need for external stabilizing agents.

The present invention provides an assay having enhanced sensitivity and simplified manufacturability compared to the membrane-based assays of the art, by using a specific combination of reagents which serve to amplify the effective binding capacity of the analyte, and enable stronger and more stable agglutination reactions. The present invention provides an assay which avoids or ameliorates the requirement for the binding partners to be pre-immobilised on the membrane.

In the presence of analyte in a sample, agglutination of the hub, analyte and second binding partner will occur, which is preferably detectable within the device The present invention is also suitable for the detection of two or more analytes within a single sample, preferably within a single assay. In such an embodiment, there may be provided two or more first binding partners, each capable of binding a different analyte. These may be provided on a single carrier, thereby producing a hub to which two or more analytes may bind. Alternatively, and preferably, the two or more first binding partners may be each provided on a separate carrier, such that two or more hubs are produced each being specific for a different epitope. In addition, a corresponding number of second binding partners are provided, each being specific for a different epitope, and each being bound to or capable of binding a detectable particle. Preferably, different detectable particles are provided for each epitope to be detected, such that its presence or absence can be determined.

The analyte may be any moiety, preferably one which is capable of being bound by a binding partner. To enable the formation of an agglutinate with a hub and second binding partner, analytes detectable in the present invention are those having at least two binding sites, or epitopes, to which a binding partner may bind. A non-limiting selection of analytes include nucleic acid, antigen, antibody, oligonucleotide, hormone, hormone receptor, vitamin, steroid, metabolite, aptamer, sugar, peptide, polypeptide, protein, glycoprotein, organism (such as fungus, bacteria, viruses, protozoa and multicellular parasites), therapeutic or non-therapeutic drugs, or any combination or fragment thereof. Preferably, the analyte may be an immunologically active protein or polypeptide, such as an antigenic polypeptide or protein. Most preferred analytes for detection by the present invention include hCG, LH, FSH, and antibodies to HIV. As will be clear to those of skill in the art, antibodies are particularly important analytes where evidence of an immune reaction is being measured. Accurate measurement of serum titres of particular antibodies is therefore an important aspect of the invention. In such assays, it will be understood that the analyte-binding reagent used is usually an antigen to which the antibodies being measured specifically bind.

The amplification of the effective binding capacity of an analyte is achieved by the use of a hub, to which two or more first binding partners capable of binding to a first epitope of the analyte are bound. The hub may be formed of any suitable material, which is preferably uniform, stable and to which binding partners can be attached. The hub may be soluble or insoluble, although the former is preferred. Examples of hubs include polystyrene latex beads, glass beads, gold sol, cells, for example red blood cells, fibrous materials such as cellulose, and macromolecules such as polysaccharides and proteins. Preferred hubs are polysaccharides, including dextran, preferably aminodextran, agarose, microcrystalline cellulose, starch. Other suitable materials include polyethyleneimine, polyvinyltoluene, or styrenebutadiamine copolymers, polyacrolein microspheres, polyurethane, pollen particles, sporopollenin, polystyrene or polyvinylnapthalene cores surrounded by shells of polyclycidyl methacrylate, microcrystalline cellulose or combinations thereof, polyvinyl alcohol, copolymers of hydroxyethyl methacrylate and methyl methacrylate, silicones and silica, glass, rubber, nylon, diatomaceous earth, silica, etc. Soluble hubs have the advantage of low non-specific binding and increased flexibility, and increased availability of groups for covalent coupling of antibodies or other binding molecules thereto. Preferred soluble hubs are soluble proteins and polysaccharides, including those described above and in particular aminodextran and derivatives thereof. The size of the hub is dictated by factors such as the number of binding partners to be accommodated on the surface, steric factors to ensure stability of the hub throughout the assay, and the nature of the porous carrier in which the assay is to be performed. For example, the hub is preferably small enough to travel through the smallest pores of a membrane in the absence of an agglutination event. Where the hub is formed of insoluble beads, these will be in the region of 0.03-10 μm diameter, preferably 0.05 to 8 μm. For soluble hubs, these may be in the region of 250-2,500 kDa, more preferably 500-2500 kDa for example for aminodextran molecules.

On the surface of the hub are first binding partners which are capable of binding a first epitope of an analyte. Thus, in the presence of analyte, the hub may bind thereto via the first binding partners on its surface. This effectively groups together a number of analyte molecules for presentation to the second binding partner. Thus, an assay using the hub and second binding partner has the potential for greater sensitivity and increased application.

In order for the hub to be effective, it is therefore preferred that at least two first binding partners directed against a particular epitope of an analyte are present on its surface. However, the greater the number of binding partners against any particular epitope on the surface of the hub, the greater the number of possible interactions with the analyte and second binding partner there will be, and thus the greater the possible size of the agglutinate. Thus, the optimal number of binding partners on the surface of the hub will be that which maintains assay sensitivity whilst minimizing any steric interference between binding partners or between the hub and second binding partner.

The first binding partners coupled to the hub may be capable of binding or being directed against, any epitope of an analyte, provided that this epitope is different to the epitope targeted by the second binding partner. Where the assay is being used for detection of a single analyte, it may be preferred that all first binding partners coupled to the hub are capable of binding the same epitope of the analyte and preferably are substantially the same. However, in embodiments of the invention where it is desired to detect two or more analytes in a single sample or assay, first binding partners capable of binding each epitope to be detected may be provided in the same hub or on different hubs.

The second binding partner is capable of binding a second epitope of the analyte and being bound or capable of binding a detectable particle, preferably simultaneously. The second binding partner preferably targets a different epitope on the analyte to that targeted by the corresponding first binding partner. The second binding partner may be coupled to the detectable particle in a number of direct or indirect ways. In one embodiment a second binding partner is coupled to a third binding partner in a bifunctional conjugate, capable of binding to both an epitope of the analyte and to the detectable particle in a specific or non-specific manner. Where the binding partners are antibodies or functional fragments or derivatives thereof, the third binding partner may specifically bind an epitope presented the surface of the detectable particle directly. In one embodiment, the detectable particle is a red blood cell and so the third binding partner may be an antibody specific for a red blood cell surface antigen.

In the context of the present invention, an epitope is a single site upon the analyte to which a binding partner is capable of binding. Thus, the epitopes bound by the binding partners described herein may conceivably be on the same or different molecule. Preferably for steric reasons, it is preferable that the first and second epitopes of the analyte, recognized by the first and second binding partners respectively, are present on sterically separate sites. Where the analyte has two or more domains, then in order to avoid steric hindrance, it is most preferable that the second binding partner recognizes an epitope on a different domain to that of the first binding partner of the hub. For example, in the case of hCG, the second binding partner is directed against an epitope on the beta chain, and the hub is directed against an epitope on the alpha chain.

The analyte epitope targeted by the first and/or the second binding partner is preferably specific for that analyte, so that binding of both the first and second binding partners to the analyte occurs only in the presence of that analyte.

In order that agglutination between a hub, analyte and second binding partner is detectable, it is preferable for the second binding partner to be capable of binding both analyte and detectable particle simultaneously. Thus, where the detectable particle becomes bound during the assay, the binding site on the second binding partner for the detectable particle is preferably sufficiently distant from the analyte binding site to enable simultaneous binding of the analyte and detectable particle. Where the second binding partner is bound to the detectable particle prior to the assay, the binding partner is preferably attached to the detectable particle such that it is still capable of binding the analyte. The detectable particle may be bound to the second binding partner by any suitable means, as described below The binding partners may be bound, or be immobilized onto, a non-target moiety, such as the hub or detectable particle, in any suitable manner, covalent or non-covalent. Binding, in particular where the detectable particle becomes bound to the second binding partner during the assay, may typically be formed between a binding site on the binding partner and an epitope (or determinant) on the hub or detectable particle. Such a determinant is preferably inherently present on the hub or detectable particle, but may be extrinsic thereto. Preferably, it is a surface protein, preferably glycophorin. Suitable means include covalent links such as for example, chemical coupling, or by non-covalent links such as antibody-antigen interactions, biotin-streptavidin, protein-protein interactions, protein G or protein A interactions, or passive adsorption. Where a covalent link is used, this will typically be between a suitable residue of the binding molecule distal to the binding site and a suitably accessible portion of a molecule of the hub. Preferably, the covalent link is formed between an amino acid, typically an amino acid side chain, such as an amino, sulphydryl, carboxyl, phenolic or other heteroaromatic or aromatic side chain.

To achieve non-covalent binding as described above, the binding partners may be provided as conjugates, wherein the binding partners hereinbefore described are coupled to a further binding partner capable of binding the hub/detectable particle. This binding preferably via sites distal to their analyte binding sites such that any interference with analyte binding is avoided. Where the binding partners are antibodies, such sites may be the tails of the binding partners such that coupling occurs in a tail-tail manner.

The coupling may be covalent, for example via amino, sulphydryl carboxyl, phenolic or other heteroaromatic or aromatic side groups of an amino acid of the binding partner, or preferably via a thiol group. Alternatively, the coupling may be non-covalent, as described above.

The binding partners of the present invention may be any substance which is capable of binding a predetermined target (such as an analyte or detectable particle) and preferably which has a preferential affinity for said predetermined target (i.e. is specific for that target). Binding partners therefore include monoclonal or polyclonal antibodies, antigens, proteins including enzymes or other binding proteins, receptors, aptamers, oligonucleotides, sugars, and fragments thereof. The binding partners are selected from the above based upon the nature of analyte and agglutinable particle, such that they are capable of binding each, as appropriate. Preferably, the binding partners may be an antibody, such as a known immunoglobulin, e.g., IgG, IgM, and the like, or monovalent and divalent antibody fragments of IgG, conventionally known as Fab and Fab', and (Fab')$_2$, respectively, or a fragment thereof. Preferably, the antibody will commonly be a divalent antibody fragment [(Fab')$_2$] or, more preferably, a monovalent antibody fragment (Fab or Fab').

Whilst it is preferred that the binding partners bind their targets directly, this is not strictly necessary, and the binding may take place via an intermediate, such as an analyte binding molecule. The intermediate might be naturally present in a sample, or may be separately provided. These include receptors, antibodies, antigens, binding molecules, hormone receptors, oligonucleotides, sugars, or aptamers, as described above in relation to the binding partners etc.

The detectable particle may be biological or non-biological, and extrinsic to the sample to be analysed, or naturally present within the sample. By 'detectable' is meant that its presence and/or location within the porous carrier is determinable, using any suitable means, either in the presence or absence of agglutination. Preferably, the particle is one which is inherently detectable, i.e, the detection of which is based upon an inherent feature of the particle (such as colour) rather than its effect on external factors. Thus, the detectable particle enables the presence and location of an agglutination to be observed, without the need to measure or assess factors external to the agglutination such as rate of flow or absorbance. Detection may be such as performed visually or calorimetrically, or by any other suitable method. Examples of detectable particles include microorganisms, cells (such as red blood cells), macromolecules, metal sol particles (such as gold or silver), beads, (preferably polystyrene latex), charcoal, kaolinite, or bentonite. Where the particle is biological and extrinsic to the sample, then it may be derived from any suitable source, and optionally prior to use may undergo any necessary pre-treatment such as washing, fixing, preserving. In the case of red blood cells, these may be derived from any suitable source, preferably an animal such as guinea pig or turkey. Red blood cells may be coated with antibody, and/or preserved, or fixed, using any suitable method. The 'label' which allows the particle to be detected may be an inherent part of the particle, or may be attached to the agglutinable particle using methods described herein. Preferably for whole blood assays, the detectable particles are the red blood cells intrinsic to the sample (suitably treated to prevent coagulation by, for example, citration).

Preferably, the detectable particle is also agglutinable, meaning that it will agglutinate, or form aggregates, with other (preferably similar or identical) detectable particles. The ability of the detectable particles to agglutinate enables the formation of larger agglutinates, preferably including two or more hubs, thus facilitating detection and increasing stability.

In view of the enhanced stability of the agglutinated complex using the reagents of the invention, a first embodiment of the invention is to perform the reaction within a capillary device. Each reagent may be placed at one or more predetermined positions in the device, and again it may be preferable for the reagents to be placed at the same position(s), or for them to be applied at separate positions. In the latter case, it is preferred for the hub to be upstream of the conjugate.

In the presence of analyte, agglutination occurs leading to arrest of fluid flow along the pathway or a decrease in the rate of flow. This can be detected by the time taken for the fluid to reach a set point or points, or the distance travelled by the fluid within a set time. Presence of fluid at set points can be detected by any means, which include, but are not limited to, visual detection of flow, clump formation, colour change etc; optical means such as reflectometers, measurement of light scattering; fluid detection; turbidometry; electrical means and nephelometry. Non-visual detection means are preferred, meaning that presence or absence of sample at the detection regions is determined by means other than the naked eye. This reduces the effect of human error, and also, in a point-of-care environment, means that continued monitoring during the performance of an assay by the user is not necessary. Further, the result is permanent and stable. Preferred detections means include the electronic optical detection means which may, for example, comprise an array of Light Dependent Diodes (LDDs) or Light Sensitive Resistors. It will be appreciated that, depending on the analyte being determined by the assay, certain of the light sensitive elements will receive light (i.e. those at the detection regions of capillaries along which sample flow has not been arrested). Software is associated with the electronic optical detector which allows the analyte to be determined from the particular signals provided by the electronic optical detector.

Conveniently, the preferred electronic optical detector is of the type used for reading barcodes by light transmission (as opposed to light reflection). In such an embodiment, predetermined regions of the reaction device (detection regions) may be optically transparent so that the presence or otherwise of sample at a detection region may be determined by providing a source of illumination on one side of the reaction device and electronic optical detector on the other side of the device. Conveniently the reaction device may be produced from a light transparent material (e.g. polycarbonate).

The detection means may be programmed to detect the presence of sample reaching a detection region by way of confirmation that the device is functioning properly. Put another way, if sample is not detected in a detection region of a capillary pathway, typically a control capillary, then it must be assumed that the reaction device is not functioning correctly so that the test will need to be repeated with a fresh device. It is also preferred to include detection means to detect the presence of sample at an upstream region of the capillary pathways to ensure that the sample has entered these pathways, again by way of a confirmation that the device is functioning properly.

The reaction device in which the assay of the invention is performed is a receptacle, as described above, and typically is hand-held. It will preferably be a single-use type device, so that it is used for the performance of one assay and then discarded.

The device may comprise one or more capillary pathways in which the assay is performed. Preferably, two capillary pathways are provided, one being the assay pathway and the other being a control pathway. However, it is envisaged that additional pathways may be provided, where it is desired, or necessary, to test a single sample for multiple analytes.

Each capillary pathway has an upstream and a downstream end, and preferably has a zone or well at the upstream end to receive sample/reagents. The zone may comprise a pad to which the sample/reagents are applied, and from which they enter the capillary pathway. The pad may be formed of absorbent material, preferably fibrous material, e.g. cellulose. Fibrous pads may exert a counter capillary force to the capillary channel and the selection of pad material will depend on the dimensions of the capillary channel since these determine the capillary force. Alternatively, a one-way valve may be provided in the zone at the entrance to the capillary pathway, so that the sample/reagents applied to the zone can enter, but not exit, the pathway upon opening of the valve. Alternatively, a pipette or other suitable device may be used to apply the liquids directly into the pathway.

As in some known capillary based agglutination assays, such as WO04/083859, the pathway may comprise the agglutination reagents at a pre-determined point in the pathway. Preferably, this will be any part of the device which comes into contact with the sample, and therefore may be all or part of the zone or a capillary pathway, preferably upstream of any points at which fluid is to be detected. All the reagents may be mixed and placed at one or more points in the capillary, or be placed separately at different points. Retardation of flow will begin, in the presence of analyte, when the fluids reach the downstream-most reagent. Typically, the rate of flow along a capillary pathway will be measured against a control sample in a neighbouring capillary pathway, the control sample not being capable of agglutination (for example due to absence of the analyte).

In an alternative method, the reagents may be added at the upstream end of the capillary pathway, at the same place as the sample, either with or before the sample. The reagents may be pre-mixed, or added separately. It is preferred for the reagent comprising the hub to be placed in the capillary upstream of the reagent comprising the conjugate. To determine whether analyte is present, a change in flow rate compared to a standard is monitored.

The pathway of the reaction device is preferably a capillary. It may be made of any suitable material, preferably the same as that of the remainder of the reaction device, such as polycarbonate, polystyrene, or injection moulded plastic, optionally transparent. The capillary pathways are preferably formed as open-topped channels in the surface of the unit, and closed by a fixing of membrane (e.g. of polyester), or seal, thereto, which is preferably hydrophilic in nature. This may be affixed to the body of the device by any suitable means, such as a hydrophilic adhesive, most preferably one that does not "outgas" or "creep". Any means used preferably do not contain components (e.g. cyanides) that denature proteins otherwise the function of the device may be impaired.

The plastics material from which the device is moulded may be hydrophobic, with the capillary pathways being optionally treated during manufacture with a hydrophilic reagent, e.g. by washing in a 0.1-10% of Tween 20. The agglutination and other reagents may then be provided in the open-topped pathways.

The reaction device may comprise the detection means and/or means for interpreting the signal provided by the detection means. Typically, these will include signal processing means which process the result for display, and display means. Thus, there may be provided an integrated device, comprising all means required for testing, signal processing and display. Alternatively, a separate reader may be provided which comprises signal processing and/or display means, and optionally detection means for determining the presence or absence of sample at pre-determined positions in the reaction device, herein defined as detection regions. Thus, whilst the reaction device needs disposing of, the signal processing/display device can be re-used. This reduces both cost of the assay and waste.

Where a separate reader is provided, it may be removably and operably attached to the reaction device, by any suitable means, in a manner which allows the results from each detection means to be obtained and analysed. Preferably, the reaction device is releasably mountable in a reader such that upon performance of an assay, the reader and reaction device become a temporarily integrated device. Thus, the reader and/or reaction device comprise means, or are arranged such that, upon mounting the detection means can communicate with detection regions in the reaction device, preferably through contact. Although not strictly necessary, the means on one or both of the reaction device and reader may allow for engagement of the components, for example by a securing or locking mechanism. In a simple embodiment, the means comprise in the test device a formation (e.g. a step formation) for locating the unit on a cooperating step in the reader.

Where the detection means are provided as part of the reaction device, they may be present at one or more suitable predetermined positions. In a capillary based reaction device, each capillary pathway may be provided with detection means, appropriate to the detection method used in the assay, as described above. Detection means may be provided at one or more positions along the capillary pathway and at least at a downstream region of a pathway, such that a quantitative result regarding the analyte in a sample is obtained by measuring the rate of flow along the capillary. Thus, the greater the amount of analyte in a sample, the stronger the agglutination reaction will be, and the slower the rate of flow along the pathway. By providing two or more detection means along the pathway, and measuring the time taken for the sample to reach each, the rate of flow can be determined. An estimate of the amount of analyte can be made by comparing the rate of flow to a calibration chart.

The detection means will detect the presence or absence of any liquid present in a detection region. The liquid will typically be a reagent and/or sample as described herein, but may include other test liquids used for control purposes or to determine the operability of the unit.

The detection means communicate with one or more of the detection regions in a capillary pathway, to determine the presence or absence of liquid. The results obtained, in the form of a yes/no indication for each detection region, form a pattern which is interpreted by the electronic means into presence and/or amount of analyte. The length of the capillary pathway will be dictated by the time scale of the agglutination reaction, in combination with factors such as the internal cross sectional area of the pathway and the nature and flow rate of the sample and reagents. It must have at least sufficient length to allow time for an agglutination reaction to take place, if analyte is present. Typically, the length of the pathway will be in the region of 30-500 mm, more preferably 35-45 cm. The capillary pathways may have any cross-section, such as circular, square or triangular, based upon manufacturing and flow criteria. The pathways may, in section, be in the form of an equilateral triangle with a side length of 50 to 1000 µm.

For convenience, the pathway may not necessarily be linear, but may take any form to suit the size and shape of the reaction device. Thus, the pathway may take a series of bends or curves along its length. Whilst any form which allows flow of the reagents/sample is acceptable, a preferred form comprises a series of parallel linear pathways connected by 180 degree bends. Where two or more pathways are provided, these may run in parallel alongside each other, allowing an easy visual monitoring of the flow, or may be provided as separate formations on the device.

A fluid may be provided to aid flow of the reagents/sample along the capillary pathway, or to increase the volume of the reaction or provide additional reagents such as electrolytes as previously mentioned. The buffer may be added together with the reagents/sample, or separately, including after the start of the reaction (a chase buffer). Suitable fluids include buffers such as PBS pH 7.4, and physiological saline.

Where the liquid of the assay is not conductive, an electrolyte may be added, upstream of the detection means. This may be solid, causing the liquid to become conductive upon dissolution, or may be pre-dissolved, in the form of a buffer for example.

The signal processing and display means may be optionally provided with a power source or means for connection to a power source. The power source may be one which is activated by application, as described in WO04/85389. Alternatively the power source may be a conventional battery.

The signal processing means are capable of converting the results from the detection means in the reaction device to a readable output on the display means. Preferably, the signal processing means also includes a timer which is activated at an appropriate point in the test. Thus, upon connection with the reaction device, the signal processing means communicate with the detection means, converting the result to a digital or other signal. This signal is then transmitted to a display device, which will present the signal is a readable format. This may be a yes/no type result, in the form of words or signs, or may be a quantitative result providing a value which is indicative of the amount of analyte present. Preferably in the latter case, a numerical value is provided such that no further interpretation of the results is necessary. Preferably, the device is as described in PCT application No. PCT/GB2005/004166.

In a second embodiment the assay of the present invention is membrane based, meaning that the reagents are introduced onto a porous carrier, and any agglutination occurs within the carrier.

Preferably, the hub and detectable particle are different entities, preferably formed from different materials or reagents.

In an advantage of the present invention, the reagents and sample may be applied to the porous carrier in any order and in any combination and there is no requirement for immobilization of a reagent at a fixed point, unlike the lateral flow assays of the art which are generally restricted to applying sample and reagents separately and in a fixed order. Any one or more of the reagents and/or sample may be combined prior to commencement of the assay, either in a separate vessel (such as a capillary or well), or in the porous carrier itself (for example in a region of porous carrier with large pores that permit free movement of agglutinated and non-agglutinated particles). In particular, it may be preferable to combine the hub, second binding partner, and/or detectable particle prior to the assay. Any mixtures may be incubated for a short period of time, for example 1-6 minutes, preferably 2-5 minutes, prior to application to the porous carrier.

The assays of the invention may be conducted in various formats.

In an "off-line" format, reagents and sample can be reacted together prior to being introduced to the porous carrier for separation of agglutinated and non-agglutinated particles. Alternatively, the reagents and sample may be applied to the porous carrier separately, or in combinations such that the reaction takes place within the carrier. In a "wet" format, the reagents and sample are applied to the porous carrier at or immediately prior to the commencement of the assay. Alternatively, the assay may be "dry", wherein one or more of the reagents have been pre-applied to the porous carrier prior to commencement of the assay in a manner which prevents their free movement within the porous carrier until re-activation, for example by wetting. Preferably, any pre-applied reagents will be reconstituted by the sample or other fluid as it passes through the porous carrier.

Thus, as detailed above in relation to the second aspect, a device of the invention may comprise a porous carrier having a hub, second binding partner, detectable particle, and/or other reagents pre-applied thereto, preferably in dried, reconstitutable form. Such reagents may be applied together or separately, at the same or different places within the porous carrier. Pre-application onto the porous carrier may avoid disadvantages of the prior art because (i) the location does not have to be exact (in comparison to the immobilized capture line in conventional lateral flow assays, where it is critical that it be in a precise location to enable it to be read and to avoid a diffuse or unclear result) and (ii) in known lateral flow assays the immobilized capture line and labeled antibody must be applied in separate locations, requiring two passes of application apparatus, or more complex machinery. In the present invention, the reagents may be pre-mixed so only one application is necessary. Methods of pre-applying reagents to a porous carrier will be well known in the art, and include drying, desiccating, air-drying, vacuum drying, freeze-drying. Typically, this will require application of a reagent to the membrane, followed by drying for up to 18 hours at a temperature range of 25-30 C.

Thus, each reagent and sample may be added either simultaneously, or sequentially, and in any combination. When applied sequentially, it may be preferable to add the sample after the reagents, and more preferably, to add the second binding partner after the hub.

Any reagent, in particular pre-applied reagents, may be placed at one or more pre-determined positions in the porous carrier, and again it may be preferable for two or more reagents to be placed at the same position(s), or for them to be applied at separate positions. In the latter case, it is preferred for the hub to be upstream of the second binding partner.

The reagents and/or sample may be applied to the porous carrier using any suitable means, for example either by placing the porous carrier within a vessel containing one or more reagents and/or sample, or by pipetting the reagents and/or sample directly onto the carrier. Any combination of application methods may be used in a single assay.

In the presence of analyte in the sample, agglutination of the reagents occurs. Any agglutinate formed during the assay will flow along the porous carrier, toward the distal end, until movement is prevented or reduced at a pre-determined site (the detection zone) within the membrane. Typically, this will be due to the presence of means for trapping agglutinates, such as reduced pore size or any other suitable means known to persons skilled in the art not reliant on a pre-immobilised specific binding reagent. Thus, in the presence of analyte, agglutinates accumulate at the site at the detection zone, thus allowing detection. Preferably, detection of agglutination is achieved by trapping agglutinates, for example using chromatographic means. Thus, for the invention to function, it is necessary to form a strong agglutination reaction such that the strong shear forces inherent in the detection do not disrupt the agglutinate. The use of the hub enables this to be achieved in the present invention.

The pathway of the reaction device is a porous carrier, which is any suitable material which enables reagents and fluid to pass therethrough. It is preferably a solid matrix, preferably fibrous. It is preferably also flexible, capable of bonding to other porous or non-porous materials, allows for visualisation of a signal, and is preferably bibulous, thus facilitating movement of fluid therethrough by capillary action. Suitable materials include paper, glass fiber, porous plastic, scintered glass or plastic, cellulose particles, nitrocellulose, gels of agarose or other polymers, or woven materials such as cloth, nylon or other polymeric mesh material, or other fibrous materials, made either from natural or synthetic materials.

The pore size of the carrier may vary within a single strip, for example to allow for trapping of agglutinates. Preferably, the pore size of the carrier upstream of any detection zone is sufficient to allow free movement of the reagents, sample and agglutinate. At a detection zone, the pore size may be reduced, in order to prevent further movement of agglutinate along the carrier, and thus allowing its detection. Thus, the pore size at the detection zone may be smaller than any agglutinate which may specifically form in the presence of analyte to be detected, but sufficiently large to allow free movement of any non-agglutinated reagents or sample. This clearly may vary depending upon factors such as the nature of the hub, analyte and binding partners used.

All or part of the porous carrier may be pre-treated with substances which prevent or reduce non-specific binding of the reagents and/or sample to the carrier. Suitable substances include detergents such as Tween 20™, Triton X-100™, or sodium dodecylsulfate (SDS), carrier proteins such as bovine serum albumin, sugars such as sucrose, trehalose and the like, etc. These may either be added to the carrier, preferably prior to the assay, or to one or more of the reagents and sample.

The porous carrier may be any suitable size and shape, adapted to the nature of the assay to be performed. Preferably, the carrier may be in the form of a strip, having a proximal end at which reagents and sample are applied, and a distal end toward which they may flow. The size of the carrier will typically depend upon the nature of the assay and size of sample to be applied, and the desired duration of the assay. The thickness of the carrier will preferably be such that any visual signals are detectable and do not become "buried" in the carrier. Preferably, the dimensions of the carrier will be such that it may be provided within a hand-held device, for point-of-care use. Thus, where the carrier is a strip, it may preferably be no more than about 20 mm wide, preferably between about 1.0 mm and 12 mm wide, and more preferably between about 3.0 mm to 8.0 mm wide, and most preferably 5 mm wide. The length of the carrier may be dictated by the time scale of the agglutination reaction, in combination with factors such as the cross sectional area of the carrier and the nature and flow rate of the sample and reagents. It must have at least sufficient length to allow time for an agglutination reaction to take place, if analyte is present. By lengthening the portion before the separation/detection zone one can increase the time for reaction (and thus potential sensitivity), by shortening the strips one can speed up the assay. The length may generally be between about 2.0 cm and 40 cm long, preferably between about 4.0 cm and 25 cm long, more preferably between about 6.0 cm and 20 cm long and most preferably between 6 cm and 15 cm long.

If necessary, assay speed may be adjusted by the addition of viscosity-altering agents, such as starch, methyl cellulose, polyethylene glycol, albumin, etc.

The porous carrier of the invention may comprise different zones, as described herein. For example, these may include an application zone, at which the reagents and sample may be applied to the carrier, a detection zone downstream of the application zone at which any agglutinate is detected, and/or a zone at which one or more reagents are pre-applied, which will be downstream of the application zone yet upstream of a detection zone. Preferably, each zone is a physically distinct portion. These zones may all be formed from a single, continuous carrier, or may be formed from physically distinct carriers, suited to each purpose, which are fluidly connected. In the latter case, the physically distinct carriers may be located along the length of carrier or laminated in the form of layers, preferably with a small overlap, preferably in the region of 1 mm. Preferably, the application zone (or reagent release pad) acts as a support for the materials, and may be formed of any suitable material, preferably having a pore size of 0.05 µm to 500 µm, more preferably 0.1 µm to 100 µm, and most preferably 0.2 µm to 30 µm. The trapping membrane of the detection zone may be of a similar material, but having a reduced pore size in comparison to the application zone. The carrier may also comprise a wick or sink upstream of the detection zone which serves to draw fluid through the porous carrier by capillary action.

To prevent soiling of the porous carrier, or leakage of reagents, it is preferably coated on at least one side, and preferably both side, with a waterproof seal. To enable detection of the agglutinate by visual means, preferably the seal is transparent. More preferably, it can be adhered to the carrier without interfering with the nature thereof. Preferred seals include plastic laminate coatings, preferably self adhesive.

To provide rigidity, the porous carrier is preferably mounted onto a solid, non-porous support. Any suitably supportive material might be used, which does not interfere with the nature of function of the carrier. Suitable support materials include polyethylene, polypropylene, poly(4-methyl-butene), polystyrene, polymethacrylate, poly(ethylene terephthalate), nylon, poly(vinyl butyrate), glass, ceramics, metals, etc.

Preferably, and particularly where the invention is intended for use by non-skilled persons, the porous carrier may be housed in a device, or receptacle, which preferably will be hand-held. The device will preferably enclose the carrier on all sides, whilst allowing application of reagents/sample to the carrier and visualisation of any agglutination. Thus, preferably, the device comprises at least one, preferably two or more apertures, allowing visualisation of the detection zone and enabling exposure of the carrier at the application zone. In some preferred embodiments, the carrier may extend from the device at the application zone, thus facilitating application of the reagents/sample. The device may also comprise a well, or other sample receiving vessel, in fluid communication with the application zone. Alternatively, the device may comprise means to allow engagement with a separate vessel.

The device may be made of any suitable material, preferably one which is rigid, water-resistant, impermeable, lightweight, and/or does not contain components (e.g. cyanides) that denature proteins, otherwise the function of the device may be impaired. Preferably, the device is made of a plastics material. Preferably, the device will be single-use type device, so that it is used for the performance of one assay and then discarded.

The device may comprise one or more porous carriers in which the assay is performed, for example where it is desired to test multiple analytes in a single device. Where two or more carriers are provided, these may run in parallel alongside each other, allowing an easy visual monitoring of the flow, or radially disposed from a common sample application zone, etc. One or more additional carriers may be provided as control pathways.

Detection is preferably by visualization (i.e. by the naked eye) of a band or signal at the detection zone, due to accumulation of agglutinate containing detectable particles. This enables a quick reading of result, and avoids the need for ancillary equipment, such as readers and signal processing means. Non-visual detection means may also be used, and include spectrophotometry, fluorimetry, etc. The latter reduces the effect of human error, and also, in a point-of-care environment, means that continued monitoring during the performance of an assay by the user is not necessary. Further, the result is permanent and stable.

Where non-visual detection methods are used, then detectors (such as reflectometers, fluorimeters, etc) and signal processing means may be required.

Where visual detection means are used, the result may be provided as a coloured signal (for example in the form of a line at the detection zone, preferably visible to the naked eye). The nature of the signal will, of course, depend upon the label and/or detectable particle used. As well as providing a yes/no indication, the intensity or size of the signal may be used to quantify the results, for example by using a reader (electronic or otherwise, with any associated signal processing means) or, more simply, by reference to a calibration chart. Suitable methods include measurement of reflectance of the signal or absorbance, or comparison of the signal to a calibration chart, for example colour charts which give a range of intensities for any given colour, and which can be graded according to amount of analyte present.

A fluid may be provided to aid flow of the reagents/sample along the porous carrier, or to increase the volume of the reaction or provide additional reagents such as electrolytes. The buffer may be added together with the reagents/sample, or separately, including after the start of the reaction (a chase buffer). Suitable fluids include buffers such as PBS pH 7.4, and physiological saline.

Accordingly, the invention provides a kit for performing an agglutination assay for detection of an analyte in a sample, the kit comprising:
  i. a hub to which two or more first binding partners are bound, each first binding partner being capable of binding a first epitope of the analyte;
  ii. a moiety comprising a second binding partner bound to, or capable of binding, a second epitope, wherein said moiety is also bound to or capable of binding a detectable particle In one embodiment of the invention, the moiety comprising the second binding partner further comprises a third binding partner capable of binding a detectable particle. Preferably, the moiety consists of a conjugate of a second binding partner capable of binding both a second epitope of the analyte and a third binding partner capable of binding a detectable particle. In one preferred embodiment the second and third binding partners are modified antibodies or functional antigen-binding fragments thereof.

In an alternative embodiment, the second binding partner is bound to the detectable particle directly or is capable of doing so. The kit in this case therefore comprises
  i) a hub to which two or more first binding partners are bound, each first binding partner being capable of binding a first epitope of the analyte;
  ii) a second binding partner capable of binding a second epitope of the analyte and bound to, or capable of binding, a detectable particle.

In a preferred embodiment, the first and second epitopes of the analyte are different, more preferably the epitopes are present on different domains of the analyte. It is also preferred that the second binding partner binds a different epitope on the analyte to that targeted by the corresponding first binding partner. Preferably the second epitope is specific to the analyte.

In a first highly preferred embodiment, the kit is in a lateral flow format and comprises a porous carrier. It is further preferred that the porous carrier is a solid matrix, most preferably a fibrous matrix. Advantageously the porous carrier comprises a detection zone having pore size which prevents movement of agglutinate downstream of said detection zone. Preferably the pore size upstream of said detection zone is sufficient to allow free movement of the hub, second binding partner, sample and any agglutinate.

Preferably the kit is for the detection of first, second and further analytes within a single sample, comprises two or more first binding partners, each capable of binding one of a first, second and further analyte, and a two or more second binding partners, each being capable of binding one of said first, second and further analytes and each second binding partner being bound to or capable of binding a detectable particle. More preferably, each second binding partner is bound to, or capable of binding, a different detectable particle.

It is preferred that the aforementioned hub comprises a stable carrier to which first binding partners can be attached and in highly preferred embodiment the hub is soluble. More preferably the hub is of protein or polysaccharide, and most preferably it comprises aminodextran or a derivative thereof.

Alternatively, the hub is an insoluble moiety, preferably a red blood cell, polystyrene latex bead, gold sol, or insoluble macromolecule.

It is preferred that the aforementioned binding partners are selected from monoclonal or polyclonal antibodies, antigens, proteins, enzymes, receptors, aptamers, oligonucleotides, sugars, and fragments thereof.

It is highly preferred that the detectable particle is an agglutinable particle and further preferred that said agglutinable particle is included in the kit. In one preferred embodiment of the kit, the moiety comprising a second binding partner capable of binding one epitope of the analyte also comprises a third binding partner capable of binding a glycophorin molecule on an agglutinable particle, preferably a red blood cell.

Alternatively the detectable particle is a microorganism, cell, macromolecule, metal sol particle, bead, charcoal, kaolinite, or bentonite. Preferably it is a gold sol particle.

In an alternative embodiment, the kit further comprises a reaction device. Preferably the reaction device is a capillary testing device, and further preferably comprises two pathways. It is further preferred that each pathway comprises an upstream and downstream end, and wherein a zone is provided at an upstream end for application of sample of reagents. One or both reagents may be pre-applied to a pathway of the capillary device during manufacture.

The kit may further comprise one or more of detection means, signal processing means, display means and a power source, which may be an integrated part of the reaction device.

In a further aspect of the invention, an assay method is provided, in which a sample is contacted with the hub and a conjugate binding molecule, as described above, and retardation of flow is detected. Where the set of reagents are not pre-deposited and dried in the capillary pathway, they and the sample may applied to the reaction device either as a mixture, or separately. In the former case, the mixtures may be incubated for a short period of time, for example 1-6 minutes, preferably 2-5 minutes, prior to application of the mixture to the capillary pathway. Where a chase buffer is used, this may be applied after another short interval, for example two minutes. The timing of the reaction for the purpose of determining flow rates is preferably initiated upon application of a buffer. After a pre-determined period of time has elapsed, any agglutination reaction is assumed to have taken place and any control will have reached the downstream end of the capillary pathway. At this point, a read-out on the display means can be taken.

Accordingly, there is provided an agglutination assay for detection of an analyte in a sample, the assay comprising the steps of:
  i. contacting the sample with
    a) a hub to which two or more first binding partners are bound, each binding partner being capable of binding a first epitope of the analyte;
    b) a moiety comprising a second binding partner capable of binding a second epitope of the analyte, wherein said moiety is bound to or capable of binding an agglutinable particle; and
    c) a detectable particle
  ii. allowing said hub, moiety comprising a second binding partner, sample and detectable particle to react; and
  iii. detecting agglutination of the hub, conjugate, agglutinable particle and analyte.

Preferably, the moiety capable of binding a second epitope is bound to a detectable particle. Alternatively it comprises a second binding partner and further comprises a third binding partner capable of binding a detectable particle.

In this case, it preferably comprises a conjugate of said second and third binding partners.

In one embodiment, the agglutinable particles are naturally present in the sample and are preferably red blood cells. The reagents and sample may be mixed prior to application to a reaction device, and are followed after a pre-determined time by application of a buffer. It is also preferred that the the results are indicated by display means, which are read after a pre-determined period of time.

In one exemplified embodiment the invention provides an agglutination assay for detection of an analyte in a sample, the assay comprising the steps of:
  i. contacting a porous carrier with a hub to which two or more first binding partners are bound, each first binding partner being capable of binding a first epitope of the analyte; a second binding partner capable of binding a second epitope of the analyte and bound to or capable of binding a detectable particle; a sample; and/or optionally a detectable particle;
  ii. allowing said hub, second binding partner, sample and optionally said detectable particle to react, and;
  iii. detecting agglutination of the hub, second binding partner and analyte in the porous carrier, wherein agglutination indicates the presence and/or amount of analyte in the sample.

Preferably the hub, second binding partner, sample and/or detectable particle are applied to the porous carrier prior to commencement of the assay. It is highly preferred that detection of agglutination is by visualization of a band or signal.

In a third aspect of the invention, there is provided a device for an agglutination assay, comprising a porous carrier having a proximal end for receiving a sample, and a distal end toward which a sample may travel along the porous carrier, wherein the porous carrier comprises in a dried, reconstitutable form a hub to which two or more first binding partners are bound, each first binding partner being capable of binding a first epitope of the analyte.

The kit of the invention may be provided as a package, which may comprise a single reaction device and sufficient reagent for a single assay, for example for use in a point of care environment. Alternatively, a plurality of devices and sufficient reagent for the same number of assays may be provided. Preferably, in this case, the reagents for each assay are individually packaged. Optionally, materials and apparatus mentioned above may also be included in the kit, such as buffers, detectable particles, application means (such as pipettes), instructions, charts, desiccants, control samples, dyes, batteries and/or signal processing/display means.

Finally, the invention provides a device for an agglutination assay for detection of an analyte within a sample, the device comprising a porous carrier having a proximal end for receiving a sample, and a distal end toward which a sample may travel along the porous carrier, wherein the porous carrier comprises in a dried, reconstitutable form a hub to which two or more first binding partners are bound, each first binding partner being capable of binding a first epitope of the analyte.

Preferably the device comprises a second binding partner, detectable particle, and/or other reagents pre-applied to the porous carrier, preferably in dried, reconstitutable form, and is housed in a device, or receptacle, which is preferably capable of being hand-held.

The present invention is suitable for testing bodily fluid samples, such as urine, whole blood, a blood fraction such as plasma, semen, sweat, saliva, amniotic fluid, cerebrospinal fluid, pleural fluid, gingival fluid, cyst extract, and tissue extracts. Urine and blood samples are preferred. Where blood samples are assayed the blood must be treated to prevent coagulation.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The present invention will be described below by way of non-limiting examples, and with reference to the drawings, in which.

EXAMPLES

Example 1

Preparation of Soluble Hub Reagent 1

1. Desalt the anti-hCG (alpha-subunit) into 0.1 M phosphate pH 7.5 buffer, using a 1.6×15 cm G25M Sephadex column, and determine concentration and yield.
2. Activate the anti-hCG antibody, using 8 molar equivalents of NHS-PEG-MAL. Incubate the reaction mixture at 20° C. for two hours. Quench the reaction with 100 molar equivalents of glycine and desalt the maleimide-activated anti-hCG into 5 mM EDTA, PBS pH 7.3 buffer using two shots down a 1.6×15 cm G50F Sephadex column. Determine concentration and yield of activated antibody.
3. Activate a 500 kDalton aminodextran using 1000 molar equivalents of 2-Iminothiolane (2-IT). Incubate the reaction mixture at 20° C. for 110 minutes. Desalt the thiol activated aminodextran into 5 mM EDTA, PBS pH 7.3 buffer, using G25M Sephadex media. Determine incorporation ratio of thiol:aminodextran using the Ellman's assay.
4. Add 25 Molar equivalents of the maleimide-activated anti-hCG antibody to the thiol-activated aminodextran and incubate the reaction mixture at 15° C. for 16 hours. Quench the reaction mixture with 1000 equivalents of N-ethylmaleimide. Purify the conjugate on a 2.6×50 cm Superdex 200PG column using 50 mM PBS pH 7.2 buffer as eluant. Determine the concentration and yield of conjugate, then filter through a 0.2 µm Minisart filter.

Example 2

Preparation of Soluble Hub Reagent 2

1. Desalt the anti-hCG (alpha-subunit) into 0.1 M phosphate pH 7.5 buffer, using a 1.6×15 cm G25M Sephadex column, and determine concentration and yield.
2. Activate the anti-hCG antibody, using 8 molar equivalents of NHS-PEG-MAL. Incubate the reaction mixture at 20° C. for two hours. Quench the reaction with 100 molar equivalents of glycine and desalt the maleimide-activated anti-hCG into 5 mM EDTA, PBS pH 7.3 buffer using two shots down a 1.6×15 cm G50F Sephadex column. Determine concentration and yield of activated antibody.
3. Activate a 500 kDalton aminodextran using 1000 molar equivalents of 2-Iminothiolane (2-IT). Incubate the reaction mixture at 20° C. for 110 minutes. Desalt the thiol activated aminodextran into 5 mM EDTA, PBS pH 7.3 buffer, using G25M Sephadex media. Determine incorporation ratio of thiol:aminodextran using the Ellman's assay.
4. Add 25 Molar equivalents of the maleimide-activated anti-hCG antibody to the thiol-activated aminodextran and incubate the reaction mixture at 15° C. for 16 hours.
5. Coat the conjugate with 'PEG' groups using 8 molar equivalents of mPEG-SMB (10 kDaltons). Incubate the reaction mixture at 20° C. for two hours. Quench the reaction using glycine and N-ethyimaleimide. Purify the conjugate on a 2.6×50 cm Superdex 200PG column using 50 mM PBS pH 7.2 buffer as eluant. Determine the concentration and yield of conjugate, then filter through a 0.2 µm Minisart filter.

Example 3

Preparation of Membrane Strips for Tests Using Wet Reagents

Figure 1:
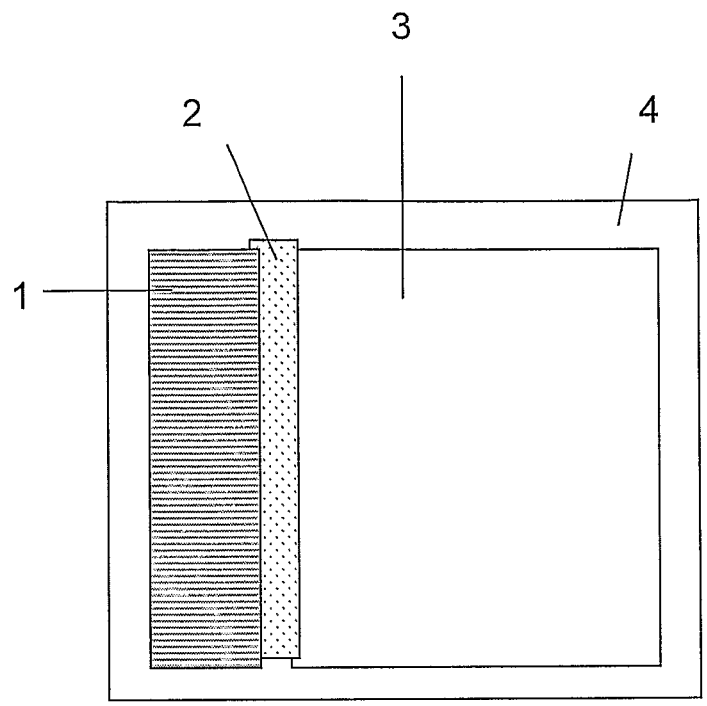
FIG. 1 shows the assembly of a membrane strip for tests using wet reagents. The labelled components are: 1, wick; 2, agglutinate-trapping membrane; 3, absorbent sink; 4, self-adhesive plastic with adhesive side facing upwards.

Membrane materials were cut to size as follows:
(i) Wick, e.g. Surewick G028-14 (Millipore), 30 mm×60 mm.
(ii) Agglutinate trapping membrane, e.g. Fusion 5 (Whatman), 5 mm×60 mm.
(iii) Absorbent sink, e.g. Absorbent Pad 222 (Ahlstrom), 55 mm×60 mm.
(iv) Self-adhesive plastic (×2) e.g. 0.04" Clear polyester with D/C hydrophilic PSA (G&L) 70 mm×100 mm A composite 'card' of the above materials was assembled as shown in FIG. 1. Adjacent membrane materials were overlapped by approximately 1 mm, to ensure good fluid transfer between successive sections of the strip. The second sheet of self-adhesive plastic was applied firmly to the upper surface. The resulting 'card' was sliced into 5 mm strips and the plastic trimmed to allow reagents and sample to enter the wick.

Example 4

Preparation of Membrane Strips Containing Desiccated Reagents

The following reagent mixture was pipetted onto a strip of conjugate release pad (e.g. Ahlstrom 8964), measuring 6 mm×50 mm.
- 75 µl anti-hCG immunogold (B.A. bHCG40, BBI)
- 50 µl anti-hCG hub reagent (prepared as described in example 1 or 2)
- 42 µl 1M Tris-HCl pH 8.2, 20% trehalose The strip was desiccated overnight at 28° C.

Absorbent sink material (GF/D, Whatman) was soaked in a solution of 0.1% tween 20. Excess fluid was removed by draining and blotting between absorbent papers, then the treated sink was desiccated overnight at 28° C.

Membrane materials were cut to size as follows:
(i) Wick (×2), e.g. Conjugate release pad 8964 (Ahistrom), 7 mm×50 mm.
(ii) Agglutinate trapping membrane, e.g. Fusion 5 (Whatman), 5 mm×50 mm.
(iii) Absorbent sink, e.g. Tween-treated GFID (Whatman), 50 mm×50 mm.
(iv) Self-adhesive plastic ('2), e.g. 0.04" Clear polyester with D/C hydrophilic PSA (G&L), 80 mm×60 mm.

Figure 2:
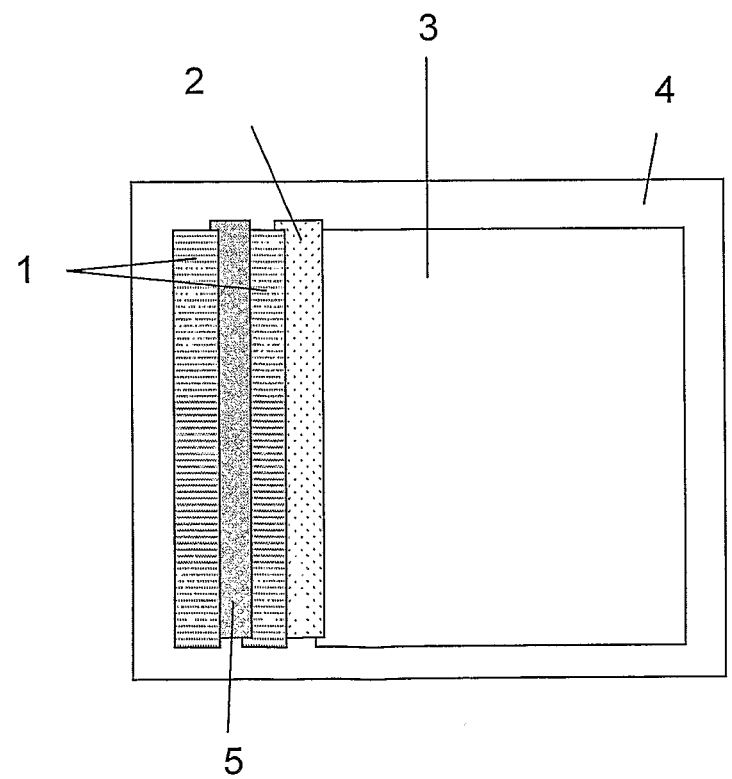
FIG. 2 shows the assembly of a membrane strip fort tests using dessicated reagents. The labelled components are: 1, wick; 2, agglutinate-trapping membrane; 3, absorbent sink; 4, self-adhesive plastic with adhesive side facing upwards; 5, pad containing desiccated reagents.
Figure 3:
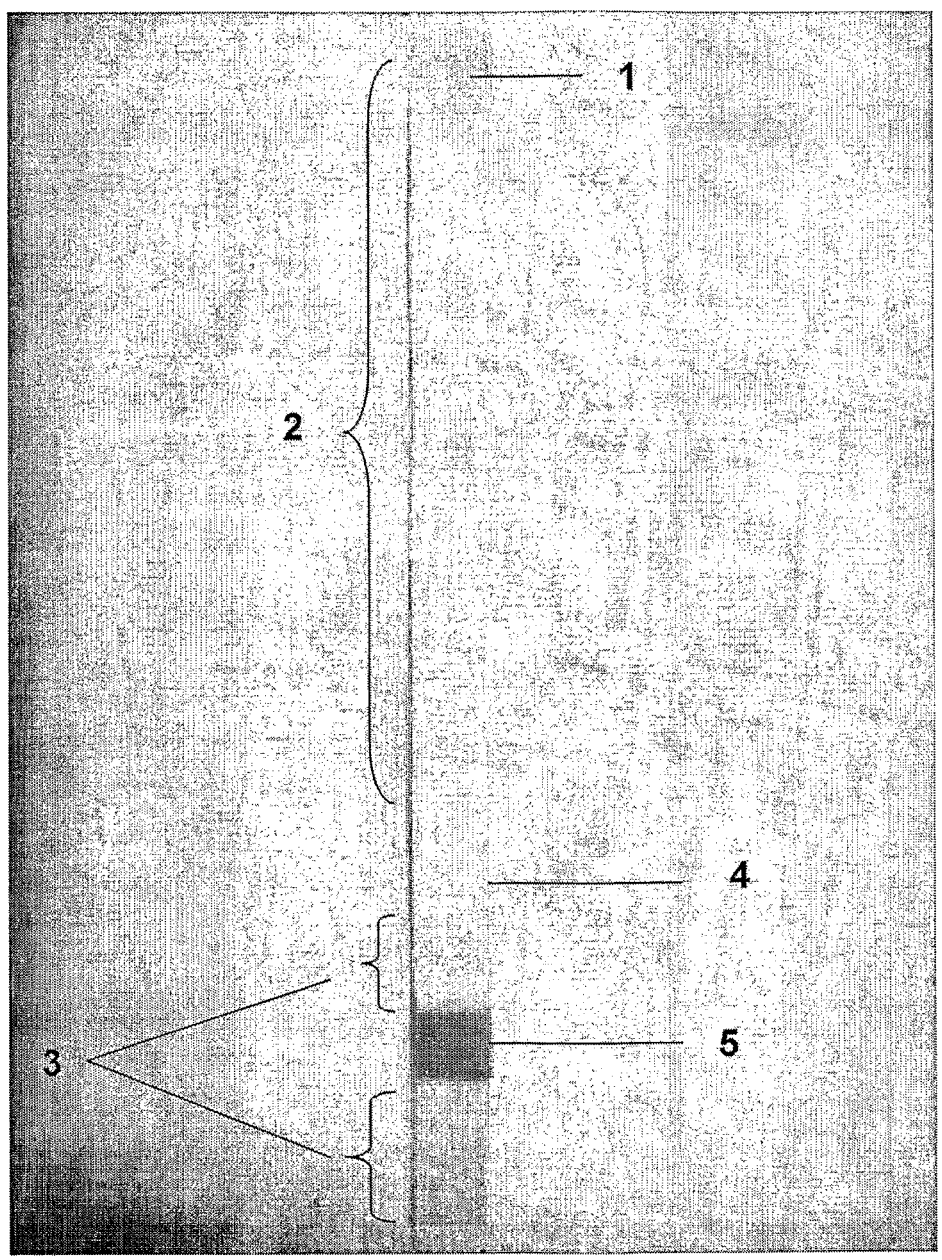
FIG. 3 shows an example of a membrane strip. Labelled components are: 1, laminated seal covering entire membrane strip; 2, absorbent wick GFD treated with 0.1% Tween®; 3, wick (Ahlstrom grade 8964); 4, Fusion 5 capture membrane; 5, reagent release pad containing desiccated reagents.
Figure 4:
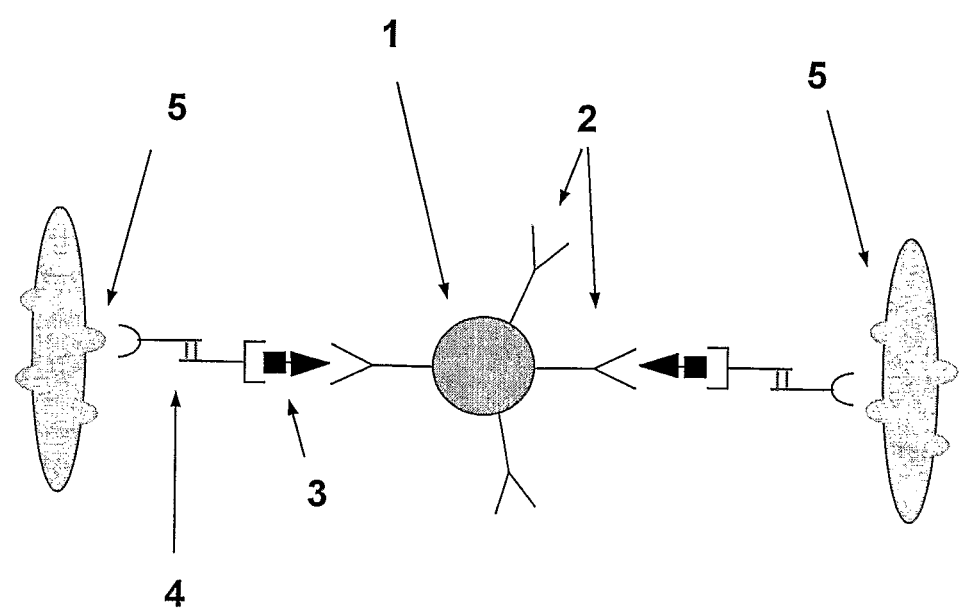
FIG. 4 shows a schematic representation of one aspect of the invention, an agglutination assay based on a hub (1), presenting a first binding partner (2, for example anti-human chorionic gonadotrophin or anti-hCG), capable of binding a first epitope of an analyte (3, for example hCG, comprising alpha and beta subunits), a moiety (4) comprising a conjugate of a second binding partner capable of binding a second epitope of the analyte together with a third binding partner capable of binding a detectable particle, in this case a red blood cell (5) bearing glycophorin antigenic determinants to which the third binding partner specifically binds. All the components then form a stable agglutination product.

A composite 'card' of the above materials was assembled as shown in FIG. 2. Adjacent membrane materials were overlapped by approximately 1 mm, to ensure good fluid transfer between successive sections of the strip. The second sheet of self-adhesive plastic was applied firmly to the upper surface. The resulting 'card' was sliced into 5 mm strips and the plastic trimmed to allow sample to enter the wick.

Example 5 hCG Test Using Wet Reagents

The following reagent mixtures were combined in a microfuge tube, then applied to the wick end of a membrane strip (prepared as described in example 3).
- 5 µl anti-hCG immunogold (B.A. bHCG40, BBI)
- 5 µl anti-hCG hub reagent (prepared as described in example 1)

The wick end of the strip was immersed in 250 µl 0.01 M PBS pH7.4, 0.1% BSA containing 0-25 IU/ml hCG with the strip orientated vertically (hCG concentration value assigned against $4^{th}$ I.S., NIBSC). When tests were complete, i.e. fluid had reached the top of the strip, the coloured signal at the agglutinate trapping membrane was compared with a standard colour chart (Dulux colour range FR4, 50RR83/040-62RR21/444) and the signal assigned a value on a scale of ± to +++++. A digital photograph was taken, to record the appearance of freshly-run tests).

The following results were obtained:

TABLE 1

| HCG Conc. mIU/ml | Signal |
|---|---|
| 0 | +/− |
| 250 | + |

TABLE 1-continued

| HCG Conc. mIU/ml | Signal |
|---|---|
| 5 000 | + |
| 25 000 | ++ |

Example 6 hCG Test Using Desiccated Reagents (Hub Reagent 1)

Membrane strips containing desiccated reagents were prepared as described in example 4, using hub reagent 1 (see example 1). Tests were performed by immersing the wick end of each strip in a simulated sample (synthetic urine) containing 0-25 IU/ml hCG, and allowing to run with the strip orientated vertically (hCG concentration value assigned against $4^{th}$ I.S., NIBSC).

When tests were complete, i.e. fluid had reached the top of the strip, the coloured signal at the agglutinate trapping membrane was compared with a standard colour chart (Dulux colour range FR4, 50RR83/040-62RR21/444) and the signal assigned a value on a scale of ± to +++++. A digital photograph was taken, to record the appearance of freshly-run tests.

The following results were obtained:

TABLE 2

| HCG Conc. mIU/ml | Signal |
|---|---|
| 0 | +/− |
| 25 | + |
| 250 | + |
| 1 000 | ++ |
| 5 000 | ++ |
| 25 000 | +++ |

Example 7 hCG Test Using Desiccated Reagents (Hub Reagent 2)

Membrane strips containing desiccated reagents were prepared as described in example 4, using hub reagent 2 (see example 2). Tests were performed as described in example 6. The following results were obtained:

TABLE 3

| HCG Conc. mIU/ml | Signal |
|---|---|
| 0 | +/− |
| 25 | + |
| 250 | + |
| 1 000 | +++ |
| 5 000 | +++ |
| 25 000 | +++ |

Example 8

Summary of Test for hCG

The immunogold and anti-hCG hub reagent mixture was premixed with buffer/additives and pipetted onto a strip of reagent release pad (e.g. Ahlstrom 8964), measuring 6 mm×50 mm. The strips were placed in a sealed container, with desiccant and humidity indicator, and allowed to desiccate overnight at 28° C.

Strips of reagent release pad, capture membrane, laminated seal and absorbent sink were cut to size using a guillotine. Membrane cards were assembled on the glue side of the laminated seal, with adjacent strip components overlapping by 1 mm (see FIG. 2). A second piece of laminated seal was used to completely seal the membrane strips.

The resulting membrane cards were cut carefully with scissors into 5 mm width strips, ensuring that the lamination around the absorbent sink did not spring open.

250 µl aliquots of the hCG solution to be tested (simulated urine sample) was pipetted into the wells of a microtitre plate. The reagent release pad end of the membrane strip was immersed in the hCG solution, keeping the strip aligned vertically. The solution was allowed to run to the very end of the membrane strip. This process was repeated for each hCG concentrations to be tested. The used membrane strips were placed onto a piece of Whatman 1 filter paper in order to see the signal clearly. Signal intensity was assigned as described in example 5 and a digital photograph taken. The filter paper was then placed on to tissue culture tray and left to dry at 28° C.

Example 9

(i) Anti-hCG beta and anti-glycophorin antibodies were desalted into 0.1M phosphate buffer pH 7.5, using G25M Sephadex media.

(ii) 8 molar equivalents of 4-(N-Maleimidomethyl)cyclohexanecarboxylic acid N-hydroxysuccinimide ester (SMCC) was added to the anti-glycophorin antibody and the reaction incubated at 20° C. for 70 minutes. The reaction was quenched using 100 molar equivalents of glycine and the maleimide-activated anti-glycophorin antibody was desalted into 5 mM EDTA, PBS buffer pH 6.5, using G25M Sephadex media.

(iii) 2.0 molar equivalents of N-succinimidyl S-acetylthioacetate (SATA) were added to the anti hCG antibody and the reaction mixture was incubated at 20° C. for 75 minutes. The reaction was quenched using 50 mM EDTA, 2.5M hydroxylamine buffer pH 7.0. The thiol-activated anti-hCG antibody was desalted into 5 mM EDTA, PBS buffer pH 6.5, using G25M Sephadex media and the incorporation ratio of thiol: antibody was determined.

(iv) 5 molar equivalents of thiol-activated anti-hCG antibody was added to the maleimide-activated anti-glycophorin antibody and the mixture incubated at 2-8° C. for 17 hours. The reaction mixture was quenched with N-ethylmaleimide and the anti-glycophorin: anti-hCG conjugate was purified on Superdex 200PG media using 10 mM PBS buffer pH 7.2 as eluant. The conjugate concentration was determine via the UV abs280 nm. Proclin 300 was added to 1% (w/w) and the conjugate filtered to 0.2 µm.

Example 10

Preparation of Reagent 3 Utilising an Insoluble Hub (Latex Particles)

(i) Anti-hCG alpha antibodies were passively adsorbed to 3 µm polystyrene latex microspheres at 10× surface binding capacity, in 10 mM phosphate buffer pH 7.4 containing 20% ethanol for 2 hours with mixing.

(ii) Surplus surface binding sites were blocked with 1% BSA, for 1 hour.

(iii) Microspheres were pelleted by centrifugation at 7000×g for 10 minutes, then washed 3× in latex dilution buffer (HEPES pH 7.4).

(iv) Antibody adsorption was confirmed by alkaline phosphatase assay, in conjunction with an hCG-alkaline phosphatase conjugate, and by slide agglutination assay, mixed with anti-hCG beta latex and hCG.

Example 10

Preparation of Reagent 3 Utilising a Soluble Hub (Streptavidin Complex)

(i) Streptavidin and biotinylated anti-hCG antibodies were combined in 10 mM PBS pH 7.4/0.1% BSA and incubated for 2 hours at 4° C. to allow formation of complexes.

Example 11

Method of Preparing the Capillary Test Device

Capillary devices disclosed in WO200408359 were prepared, prior to reagent deposition, by cleaning in 50% ethanol with sonication, followed by washing in a solution of Tween 20, to render the surfaces hydrophilic. Tween-treated test devices were desiccated and sealed using pressure-sensitive adhesive tape before use.

Example 12

Method of Performing a Slide Agglutination Test

Human blood (20 µl, spiked with desired concentrations of hCG) was mixed with an equal volume of soluble 'hub' complex (reagent 3, example 3) and 5 µl of reagent 1 (0.1 mg/ml). After 2-5 minutes 20 µl of the mixture was transferred to a glass microscope slide and rocked/rotated for 30 seconds. Reaction mixtures were viewed at 100× magnification and the extent of agglutination assessed.

The following results were obtained:

TABLE 4

| hCG Concentration | Agglutination Intensity |
|---|---|
| 0 mIU/ml | +/− |
| 570 mIU/ml | + |
| 5,700 mIU/ml | +++ |

Example 13

Capillary Agglutination Test Using Insoluble Hub Reagents

Capillary devices were prepared according to Example 4.
Reagent 1 was prepared according to Example 1
Reagent 3 was prepared according to Example 2.
Reaction mixtures were assembled as follows:
60 µl anti-hCG alpha latex 3% suspension (reagent 1)
60 µl human whole blood containing hCG
15 µl antibody conjugate (99 ng/µl) (reagent 3)
Reaction mixtures were incubated for 2-5 minutes, then 20 µl was introduced, by manual pipetting, to the capillary entrances in the fluid reservoir of the test device. Fluid mixtures were subsequently drawn into the beginning of each capillary track by capillary force. A timer was started and 2 minutes allowed to elapse, before the addition of 0.5 ml PBS pH 7.4 'chase buffer' to the fluid reservoir of the test device. On addition of the 'chase buffer' a second timer was started and the time taken for the fluid mixture to reach the end of the capillary device was measured.

Example capillary run times vs hCG concentration are shown below. For each hCG concentration n=12).

Preliminary data from 'Off-line' experiments:

TABLE 5

| HCG concentration | Mean capillary run time |
|---|---|
| 0 IU/ml | 96.3 seconds |
| 0.57 IU/ml | 102.2 seconds |
| 5.7 IU/ml | 117.6 seconds |

Example 14

Capillary Agglutination Test using Soluble Hub

Reagent 1 was prepared according to Example 1
Reagent 3 was prepared according to Example 3
The Capillary Devices were prepared according to Example 4, except that prior to sealing with pressure-sensitive adhesive tape, Reagents 1 and 3 were deposited in the test capillary track of that device and dried in-situ. No reagents were placed in the control track. The device is sealed as described in WO200408359 and closed ready for use.

The method and steps to perform the reaction of the invention were as follows:
  (i) 20 µl of human blood (spiked with desired concentrations of hCG) was introduced to the start of the capillaries of a prepared test device. (The fluid was drawn into the first 10 cm of the tracks by capillary action—approximately 10 µl into each track).
  (ii) After 2 minutes, 0.5 ml of PBS was introduced to the fluid reservoir of the device. (This caused the capillary flow to resume).
  (iii) Time taken, from the introduction of PBS, for the fluids to reach the end of the capillary tracks were recorded.

Figure 5:
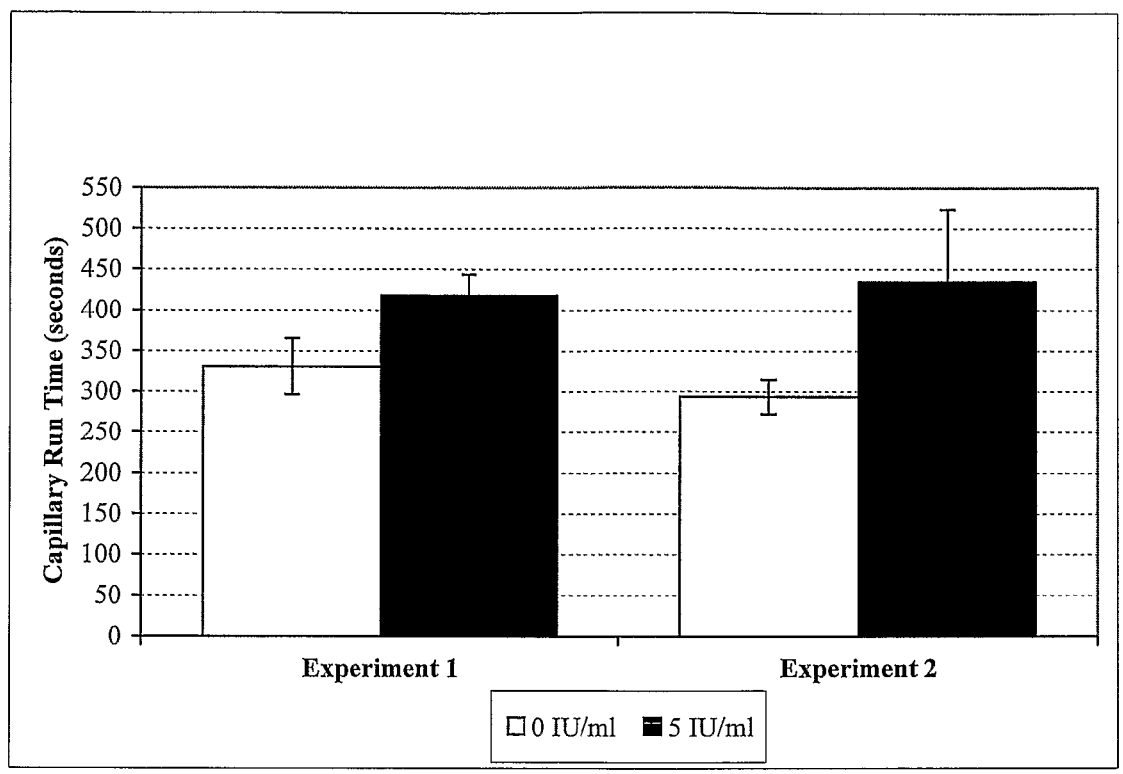
FIG. 5 shows the results from assays using soluble hubs and antibody conjugates as detailed in Example 15.

The results obtained are shown in FIG. 5:
As shown in FIG. 5, in two separate experiments, capillary run times were on average 87 (expt 1) and 141 (expt 2) seconds slower when hCG (5 IU/ml) was present in the blood sample (n=12). Error bars represent standard deviation.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A kit for performing an agglutination assay for detection of an analyte in a sample, the kit comprising:
  i. a capillary testing device having at least one capillary pathway;
  ii. a conjugate comprising a soluble hub to which two or more first binding partners are bound, wherein the soluble hub is a soluble polysaccharide having a molecular weight of 250-2,500 kDA wherein each first binding partner has a specific binding site for a first epitope of the analyte whereby upon binding the analyte is presented to the assay as a multi-epitopic entity, and wherein the conjugate is soluble in an aqueous solution; and
  iii. two or more of a first agglutinable particle each having two or more second binding partners bound to it, wherein each of the second binding partners comprises a specific binding site for a second epitope of the analyte, wherein the first and second epitopes are different from each other; and
  wherein the kit does not comprise a second agglutinable particle.

2. The kit according to claim 1, wherein each of the second binding partners comprise a third binding partner having a binding site for the first agglutinable particle and wherein the second binding partners are bound to the first particle via the third binding partner.

3. The kit according to claim 2 wherein said second and third binding partners are conjugated.

4. The kit according to claim 1, wherein the epitopes are present on different domains of the analyte.

5. The kit according to claim 1 for the detection of first, second and further analytes within a single sample, the kit comprising two or more first binding partners, each comprising a specific binding site for one of a first, second and further analyte, and two or more second binding partners, each comprising a specific binding site for one of said first, second and further analytes, wherein each second binding partner is bound to the agglutinable particle.

6. The kit according to claim 1, wherein the polysaccharide comprises aminodextran.

7. The kit according to claim 1, wherein the binding partners are selected from the group consisting of: monoclonal or polyclonal antibodies, and fragments thereof that bind the epitopes of the analyte.

8. The kit according to claim 2 wherein the binding site is specific to glycophorin and the agglutinable particle is a red blood cell.

9. The kit according to claim 1 wherein the capillary testing device comprises two pathways.

10. The kit according to claim 9 wherein each pathway comprises an upstream and downstream end, and wherein a zone is provided at an upstream end for application of sample or reagents.

11. The kit according to claim 1 wherein one or both of the conjugate and the two or more of a first agglutinable particle each having two or more second binding partners bound to it, are pre-applied to a capillary channel of the capillary testing device.

12. The kit according to claim 1, further comprising at least one component selected from the group consisting of: detection means, signal processing means, display means and a power source.

13. The kit according to claim 12, wherein the at least one component is an integrated part of the capillary testing device.

14. The kit according to claim 12, wherein the at least one component is provided in a separate reader, that is removeably and operably connectable with the capillary testing device.

15. The kit according to claim 1, further comprising one or more components selected from the group consisting of: buffers, application means, instructions, charts, desiccants, control samples, dyes, and batteries.

16. The kit according to claim 1 wherein the agglutinable particle is naturally present in the sample.

17. The kit according to claim 16 wherein the agglutinable particle is a red blood cell.

* * * * *